United States Patent [19]

Poulina et al.

[11] Patent Number: 5,681,727
[45] Date of Patent: Oct. 28, 1997

[54] PROCESS FOR PREPARING FATTY ACID ESTERS OF ALKYL GLYCOSIDES

[75] Inventors: Ramires Rolando Poulina, Gouda, Netherlands; Alasdair Robin Macrae, Bedford, United Kingdom

[73] Assignee: Unichema Chemie B.V., Gouda, Netherlands

[21] Appl. No.: 693,288

[22] PCT Filed: Feb. 15, 1995

[86] PCT No.: PCT/EP95/00505

§ 371 Date: Aug. 15, 1996

§ 102(e) Date: Aug. 15, 1996

[87] PCT Pub. No.: WO95/23871

PCT Pub. Date: Sep. 8, 1995

[30] Foreign Application Priority Data

Mar. 4, 1994 [EP] European Pat. Off. .............. 94301554

[51] Int. Cl.$^6$ .............................. C12P 19/44; C07H 15/04
[52] U.S. Cl. ........................ 435/135; 435/18; 435/134; 435/72; 435/195; 435/197; 435/198; 435/921
[58] Field of Search ........................ 435/135, 134, 435/18, 19, 195, 197, 198, 72; 536/119, 124, 115, 4.1

[56] References Cited

FOREIGN PATENT DOCUMENTS

94/01575  1/1994  WIPO .

OTHER PUBLICATIONS

Mutua et al. (1993). JAOCS, vol. 70(1): 43–46.

*Primary Examiner*—Robert A. Wax
*Assistant Examiner*—Tekchand Saidha
*Attorney, Agent, or Firm*—Cushman Darby & Cushman IP Group of Pillsbury Madison & Sutro LLP

[57] ABSTRACT

Fatty acid esters of alkyl glycosides are enzymatically prepared by forming a micro-emulsion from a fatty acid, an alkyl glycoside and a nonionic or anionic surface active agent. The viscosity of the micro-emulsion is adjusted with tertiary butanol 2-methyl-1-butanol acetone or 2-butanone. After the enzymatic esterification has been effected, the reaction mixture is subjected to pervaporation.

17 Claims, No Drawings

PROCESS FOR PREPARING FATTY ACID ESTERS OF ALKYL GLYCOSIDES

This application claims benefit of international application PCT/EP95/00555 filed Feb. 15, 1996.

The present invention relates to a process of enzymatically preparing fatty acid esters of alkyl glycosides.

Such a process is known from International Patent Application WO-A-8901480 (Novo Industri) in which alkyl glycosides having an alkyl group with 2–6 carbon atoms are reacted with a C4–C24 (preferably C6–C22) fatty acid or a lower alkyl ester thereof in the presence of a hydrolase, which preferably is a lipase, which is producable by species of Rhizomucor, Humicola, Pseudomonas or Candida. The enzymes may be applied in a soluble state or in immobilized form. It has been stated that preferably no solvent is used, but that if an organic solvent is used, it should have no deleterious effect on the enzyme. Suggested solvents are ketones (like 2-butanone), hydrocarbons (like pentane, hexane or heptane) and ethers. In two examples 2-butanone is used as a solvent in a large excess compared to the total weight of the reactants. A problem in the technical realisation of the process on an industrial scale is the high viscosity of the alkyl glycoside, which needs to be mixed with the molten fatty acid, which is very difficult, if at all possible. If the amount of fatty acid is increased relative to the alkyl glycoside to increase the reaction efficiency, side-products, such as di-ester, tend to be formed in appreciable amounts.

It has therefore been proposed in International Patent Application WO-A-941575 (Unilever) to first convert the reactants alkyl glycoside and fatty acid into a stable micro-emulsion by means of surface-active agent, which is preferably an anionic or nonionic surface-active agent. In a preferred embodiment, part of the alkyl glycoside fatty acid ester formed is recycled into the reaction to act as the surfactant in the formation of the micro-emulsion. This micro-emulsion is then subjected to the enzymatic esterification reaction, using a lipase, particularly an immobilized lipase.

It has been found, however, that even such micro-emulsions may still exhibit viscosities which are too high to pass them over a fixed bed enzyme catalyst. The convenience of working with micro-emulsions can be retained, however, if a series of interlocking process steps is applied in the enzymatic manufacture of the alkyl glycoside fatty acid esters. Thus it has been found that the viscosity of the micro-emulsions can effectively be reduced by combining the micro-emulsion with an effective amount of a specific viscosity reduction agent, after which the micro-emulsion is passed over a fixed bed hydrolase catalyst under pressure and the final reaction product obtained is subjected to pervaporation. In this way a convenient process is obtained which enables the working with normally high viscosity mixtures and which leads to high yields of the ester in an economically attractive way.

Therefore, the present invention relates to a process of enzymatically preparing fatty acid esters of alkyl glycoside in which a micro-emulsion is formed from a saturated or unsaturated, straight or branched chain fatty acid having from 6 to 22 carbon atoms, a nonionic or anionic surface active agent and an alkyl glycoside in which the alkyl group is a saturated, straight or branched chain alkyl group having from 1 to 8 carbon atoms, which is characterized in that (a) the micro-emulsion obtained is combined with an effective amount of a viscosity reducing agent, selected from the group consisting of tertiary butanol, 2-methyl-2-butanol, acetone, 2-butanone, and mixtures thereof, (b) the micro-emulsion with adjusted viscosity is contacted at least one time with a lipase at a temperature of 35° C. to 85° C. and a pressure of up to 20 bar, and (c) the reaction mixture obtained is subjected to a pervaporation treatment at a temperature of 65° C. to 100° C. and a pressure of at least 1 bar.

Preferably the fatty acid is a saturated or unsaturated, straight or branched chain fatty acid, having from 8 to 20 carbon atoms. Also mixtures of fatty acids may be used and the fatty acids may be of a technical grade. The fatty acids may also comprise functional groups, such as hydroxyl groups, amino groups and the like other groups.

The alkyl group of the alkyl glycoside is a saturated, straight or branched chain alkyl group, having from 1 to 8 carbon atoms, preferably from 1 to 4 carbon atoms.

The glycoside part of the alkyl glycoside comprises from 1 to 3 monosaccharide units. These monosaccharide units preferably are in the pentose or hexose form (particularly the furanose or pyranose form). Suitable monosaccharides are arabinose, ribose, xylose, xylulose, lyxose, ribulose and 2-deoxyribose, glucose, fructose, galactose, mannose, sorbose, talose and deoxy sugars, such as 2-deoxygalactose. Preferred disaccharides are maltose, isomaltose, cellobiose, lactose and sophorose. Also various heptoses and heptuloses, such as glucoheptose and mannoheptulose may be used. Mixtures of alkyl glycosides may also be used.

The nonionic and/or anionic surface active agent used in the manufacture of the stable micro-emulsion may be a C6–C22 fatty acid ester of glycerol, polyglycerols, sugars, sugar alcohols or alkyl glycosides, an alkali metal salt of a C6–C22 fatty acid, sodium bis (2-ethylhexyl) sulfosuccinate, alkyl polyglycosides, and mixtures thereof. Preferably the fatty acid ester of the alkyl glycoside formed in the reaction is used as the nonionic surface active agent. It has been found that particularly good results are obtained if the average chain length of the fatty acid in the alkyl glycoside fatty acid ester used as the nonionic surface active agent is the same as the average chain length of the fatty acids used as the reactant.

If alkyl glycoside fatty acid ester is used as the nonionic surface active agent the minimum amount required to form a stable micro-emulsion increases with increasing chain length of the fatty acid in the ester and if for example ethyl 6-0-lauroylglucoside is used, an amount of 3% by weight is sufficient to form a stable micro-emulsion. In general, the amount of nonionic or anionic surface active agent required to form a stable micro-emulsion is from about 1% by weight to about 10% by weight, larger amounts are possible, but economically not desirable. Sometimes smaller amounts may be used.

The combination of the viscosity reducing agent with the micro-emulsion can be effected in any suitable way, for example by dosing the required amount of the viscosity reducing agent into the micro-emulsion and passing the mixture through in-line static mixers. It has been found that there are certain optimum amounts for the various viscosity reducing agents. For 2-butanone the optimum amount is 20% to 25% by weight, for acetone the optimum amount is 20% to 35% by weight and for tertiary butanol the optimum amount is 25% to 50% by weight of the micro-emulsion. In general such an amount of the viscosity reducing agent is used so as to adjust the viscosity of the micro-emulsion to a value of 10 mPa s to 100 mPa s at 60° C., preferably 25 mPa s to 40 mPa s at 60° C.

The micro-emulsion having the required, adjusted viscosity is then contacted at least one time with a lipase at a temperature of 35° C. to 85° C. and a pressure of up to 20 bar. It is preferred that the lipase is on a carrier forming a fixed bed enzyme catalyst and it is possible to pass the micro-emulsion various times over this bed.

The lipase which has been immobilized on a carrier preferably is a lipase produced by strains such as *Rhizomucor miehei* (Lipozyme; Trade Mark, ex. Novo, Denmark), *Candida antarctica* and *Candida cylindracea*, but also other mould, yeast or bacterial lipases may be used, such as those producable by species of Humicola, Pseudomonas, and the like.

The lipase is immobilized on a carrier which may be effected by a carrier binding technique, a cross-linking technique. The carrier may be an inorganic substance like active carbon, porous glass, macroporous silica rendered hydrophobic, like XWP-1500 (Trade mark; ex W. R. Grace, USA; average particle size 0.5–1 mm; average pore size 150 nm), and the like; a natural compound, such as starch, and a synthetic, preferably macroporous, polymer such as polyolefins, like Accurel EP-100 (Trade Mark; ex AKZO, The Netherlands, having a particle size of 100 μm–1000 μm, preferably 200–500 μm and a pore size above 100 nm); anion-exchange resins like Duolite ES-568N (Trade Mark, ex. Röhm and Haas, Germany); acrylic resins, and the like. The use of macroporous polyolefin resins, like Accurel EP-100, is preferred. The polymers should be selected in such a way that they are not impaired (e.g. by swelling and/or cracking) by the solvents used in the process.

If a sufficient degree of esterification has been reached, the reaction mixture is subjected to a pervaporation treatment at a temperature of 65° C. to 100° C., preferably 70° C. to 95° C. and at a pressure of at least 1 bar. Pervaporation is a known technique and its use in enzymatic esterification has been described in European Patent Application EP-A-506,159 (Unichema Chemie BV).

In pervaporation, a liquid feed (containing a more permeable and a less permeable component) is maintained in contact with a permeable membrane and a pressure drop is maintained across the membrane. Out of the feed liquid the component to be removed, passes through the membrane. The permeate which passes through the membrane and is in vapour form, may be recovered by condensation at low temperature or may be carried away by using a moving stream of gas. Preferably, the permeate side of the membrane is maintained at low pressure in the magnitude of 5 mmHg (0.5=67 KPa). The residual feed kept in the separation unit is called the retentate or concentrate. In the process of vapour permeation, the feed mixture is first evaporated and then the vapour is passed along the membrane.

The pervaporation process has been described in a more detail in W. S. Winston Ho and K. K. Sirkar "Membrane Handbook"., van Nostrand Reinhold Publishing Corp., New York, 1992 on pages 105–159.

The pervaporation takes place across a pervaporation membrane. This membrane may be of any of the commercially available varieties, provided that they have adequate resistance to the reaction mixture. The pervaporation membrane is typically a multilayer membrane, comprising an active outer layer of (modified) polyvinyl alcohol, a porous backing layer which may be a polyacrylonitrile layer and a support layer which may be a non-woven polyester like poly (ethylene terephthalate). Also other suitable types of membranes may be used. The pressure at which the pervaporation unit is operated, depends on the pressure at which the reaction is effected in the packed bed enzyme catalyst but in general the conditions are selected thus that a maximum troughput is achieved.

The invention will now further be illustrated on the hand of the following examples.

EXAMPLE I 17.2 kg of ethyl glucoside in 31.9 kg of ethanol were mixed with 20.0 kg of lauric acid (PRIFAC 2922; Trademark, ex Unichema Chemie BV, Gouda, The Netherlands acid value 278–282, titre 43–43.7° C., iodine value 0.2) and 2.8 kg of ethyl 6-0-lauroyl-glucoside at 50° C. and then passed through a wiped film evaporator, operating at 85° C. and 90 mbar to evaporate off the bulk of the ethanol.

After leaving the film evaporator a micro-emulsion had been formed, having a viscosity of 960 mPa s at 60° C. (measured with Brookfield rotation viscosimeter). The viscosity of the stable micro-emulsion was adjusted to 30 mPa s at 60° C. by mixing the micro-emulsion with 10.0 kg of acetone. This micro-emulsion was then passed at 55° C. over a fixed bed enzyme catalyst consisting of *Candida antarctica* lipase on Accurel EP-100 (Trade Mark; Ex AKZO, Arnhem, The Netherlands). The amount of lipase used was 2% by weight of the charged feedstock and the fixed enzyme was charged in a packed bed which was kept in a holding vessel in an amount of 1 kg. The micro-emulsion was recirculated over this fixed bed lipase catalyst by means of a pump in a closed loop connected to the holding vessel. The pressure in the holding vessel containing the packed bed was 5 bar. Downstream the holding vessel a plate and frame model pervaporation unit module, Type celfa T-1 (Trade Mark; ex CELFA Membrantrenntechnik AG, Switzerland) containing 4.1 m$^2$ of CM Celfa-A membrane was provided and the reaction mixture was passed into this pervaporation unit operating at 85° C. and an inlet pressure of 4.5 bar and an outlet pressure of 4.0 bar.

A 95% conversion of ethyl 6-0-lauroylglucoside (calculated on the ethyl glucoside charged) was obtained in 12 hours. The product composition was 90% by weight of mono-ester, 2% by weight of di-ester, and the remainder was excess of lauric acid and non-converted ethyl glucoside and the product had a colour of less than 1 on the Gardner '63 scale.

EXAMPLE II

Example I was repeated, but the viscosity of the micro-emulsion was adjusted to 70 mPa s at 60° C. by adding 10 kg of tertiary butanol. The micro-emulsion was then passed through the packed bed enzyme catalyst in the holding vessel at an inlet pressure of 3 bar and an outlet pressure of 2.5 bar, the reaction being effected at 60° C. The pervaporation was effected at 95° C., an inlet pressure of 2.5 bar and an outlet pressure of 2 bar.

A 96% conversion of ethyl-6-0-lauroyl glucoside (calculated on the ethyl glucoside charged) was obtained in 20 hours. The product composition was 91% by weight of mono-ester, 2% by weight of di-ester, and the remainder was excess of lauric acid and non-converted ethyl glucoside, and the product had a colour of less than 1 on the Gardner '63 scale.

EXAMPLE III 11.4 kg of ethyl glucoside in 32.6 kg of ethanol were mixed with 18.6 kg of oleic acid and 10 kg of ethyl 6-0-oleylglucoside at 50° C. and then passed through a wiped film evaporator, operating at 85° C. and 90 mbar to evaporate off the bulk of the ethanol.

After leaving the film evaporator the viscosity of the stable micro-emulsion was adjusted to 50 mPa s at 60° C. by adding 10.0 kg of acetone. The micro-emulsion was then further treated as described in Example I, upon which a conversion of 94% of ethyl 6-0-oleylglucoside (calculated on the ethyl glucoside charged) was obtained in 12 hours. The product composition was 90.5% by weight of monoester, 1.8% by weight of di-ester and the remainder was excess of oleic acid and non-converted ethyl glucoside, and the product had a colour of 3–4 on the Gardner '63 scale.

We claim:

1. In a process of enzymatically preparing fatty acid alkyl esters of alkyl glycosides in which a micro-emulsion is formed from a fatty acid having from 6 to 22 carbon atoms, a nonionic surface active agent and an alkyl glycoside in which the alkyl group has from 1 to 8 carbon atoms and the micro-emulsion is then subjected to enzymatic esterification reaction, the improvement wherein (a) the micro-emulsion before said reaction is combined with an effective amount of a viscosity reducing agent selected from the group consisting of tertiary butanol, 2-methyl-2-butanol, acetone, 2-butanone, and mixtures thereof, (b) the micro-emulsion with the adjusted viscosity is contacted at least one time with a lipase at a temperature of 35° C. to 85° C. and a pressure of up to 20 bar, and (c) the reaction mixture obtained is subjected to a pervaporation treatment at a temperature of 65° C. to 100° C. and a pressure of at least 1 bar.

2. A process according to claim 1, in which the fatty acid is a saturated or unsaturated, straight or branched chain fatty acid having from 8 to 20 carbon atoms.

3. A process according to claim 1, in which the alkyl glycoside has a saturated, straight or branched chain alkyl group having from 1 to 4 carbon atoms.

4. A process according to claim 1, in which the alkyl glycoside has from 1 to 3 monosaccharide units.

5. A process according to claim 1, in which the nonionic surface active agent is selected from the group consisting of C6–C22 fatty acid esters of glycerol, polyglycerols, sugars, sugar alcohols and alkyl glycosides; alkali metal salts of C6–C22 fatty acids; sodium bis (2-ethylhexyl) sulfosuccinate; alkyl polyglycosides and mixtures thereof.

6. A process according to claim 1, in which the average chain length of the fatty acid radical of the alkyl glycoside ester used as nonionic surface active agent is the same as the average chain length of the fatty acid reactant.

7. A process according to claim 1, in which from 1% to 10% by weight of the micro emulsion of nonionic surface active agent is used.

8. A process according to claim 1, in which in step (a) from 20% to 25% by weight of the micro-emulsion of 2-butanone is used.

9. A process according to claim 1, in which in step (a) from 20% to 35% by weight of the micro-emulsion of acetone is used.

10. A process according to claim 1, in which in step (a) from 25% to 50% by weight of the micro-emulsion of tertiary butanol or 2-methyl-2-butanol is used.

11. A process according to claim 1, in which in step (a) the viscosity of the micro-emulsion is adjusted to 10 mPa s to 100 mPa s at 60° C.

12. A process according to claim 1, in which in step (a) the viscosity of the micro-emulsion is adjusted to 25 mPa s to 40 mPa s at 60° C.

13. A process according to claim 1, in which in step (b) the temperature is from 45° C. to 65° C.

14. A process according to claim 1, in which in step (b) the temperature is up to 10 bar.

15. A process according to claim 1, in which in step (b) the lipase is immobilized on a carrier, selected from the group consisting of macroporous silica rendered hydrophobic, macroporous polyolefins and macroporous anion-exchange resin.

16. A process according to claim 1, in which the lipase is selected from the lipases producable by *Candida antarctica*, *Candida cylindracea* and *Rhizomucor miehei*.

17. A process according to claim 1, in which in step (c) the temperature is from 70° C. to 95° C.

* * * * *